(12) United States Patent
Renshaw et al.

(10) Patent No.: US 8,897,854 B2
(45) Date of Patent: Nov. 25, 2014

(54) BRAIN PHOSPHORUS SPECTROSCOPY IN BIPOLAR DISORDER

(71) Applicant: University of Utah Research Foundation, Salt Lake City, UT (US)

(72) Inventors: Perry F. Renshaw, Salt Lake City, UT (US); Douglas G. Kondo, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 207 days.

(21) Appl. No.: 13/653,311

(22) Filed: Oct. 16, 2012

(65) Prior Publication Data

US 2013/0123605 A1 May 16, 2013

Related U.S. Application Data

(60) Provisional application No. 61/548,176, filed on Oct. 17, 2011.

(51) Int. Cl.
*A61B 5/05* (2006.01)
*A61B 5/00* (2006.01)
*A61B 5/055* (2006.01)
*A61B 5/145* (2006.01)

(52) U.S. Cl.
CPC ............... *A61B 5/055* (2013.01); *A61B 5/0042* (2013.01); *A61B 5/4076* (2013.01); *A61B 5/14546* (2013.01)
USPC .......................................................... 600/410

(58) Field of Classification Search
CPC .............................. A61B 5/055; A61B 5/4076
USPC .......................................................... 600/410
See application file for complete search history.

(56) References Cited

PUBLICATIONS

Amen, et al., "Brain SPECT Imaging in Complex Psychiatric Cases: An Evidence-Based, Underutilized Tool," The Open Neuroimaging Journal, 2011, 5, 40-48.
Burton, "Brain Scam—Why is PBS airing Dr. Daniel Amen's self-produced infomercial for the prevention of Alzheimer's Disease?" Salon.com, May 12, 2008, 5 pages.
Chang, et al., "Will neuroimaging ever be used to diagnose pediatric bipolar disorder?" Development and Psychopathology, 2006, 18, 1133-1146.
Cyranoski, "Thought Experiment," Nature, Jan. 13, 2011, 469, 148-149.

(Continued)

*Primary Examiner* — Rajeev Siripurapu
(74) *Attorney, Agent, or Firm* — James W. Hill; Douglas B. Espenschied; McDermott Will & Emery LP

(57) ABSTRACT

Described herein are systems and methods of identifying bipolar disorder in a person. One such method includes acquiring $^{31}$P spectroscopic imaging data from a region of interest in a brain of the person and subsequently analyzing the $^{31}$P spectroscopic imaging data to obtain a signal intensity and a concentration for one or more phosphorus metabolites. A reduced concentration the one or more phosphorus metabolites, such as inorganic phosphate, in the brain can indicate bipolar disorder in the person. Frontal lobe inorganic phosphate concentration in medication-free adolescents can indicate bipolar depression.

11 Claims, 6 Drawing Sheets

(56) References Cited

PUBLICATIONS

"First do no harm—Simple tools to diagnose mental illness should not be offered without sound supporting evidence." Nature, Jan. 13, 2011, 469, 132.

Phillips, "Coming of Age?: Neuroimaging Biomarkers in Youth," Am J Psychiatry, Jan. 2010, 167:1, 4-7.

Balaban, "Regulation of oxidative phosphorylation in the mammalian cell," Am J Physiol Cell Physiol, 1990; 258:C377-89.

Bose, et al., "Metabolic Network Control of Oxidative Phosphorylation: Multiple Roles of Inorganic Phosphate," J Biol Chem 2003; 278:39155-65.

Brambilla, et al., "1H magnetic resonance spectroscopy investigation of the dorsolateral prefrontal cortex in bipolar disorder patients," J Affect Disord 2005; 86:61-7.

Brazy, et al., "Does availability of inorganic phosphate regulate cellular oxidative metabolism?" News Physiol Sci 1986; 1:100-3.

Brennan, et al., "Rapid Enhancement of Glutamatergic Neurotransmisson in Bipolar Depression Following Treatment with Riluzole," Neuropsychopharmacology 2010, 35:834-6.

Brown, "Control of respiration and ATP synthesis in mammalian mitochondria and cells," Biochem J 1992; 284 ( Pt 1):1-13.

Caetano, et al., "Lower N-Acetyl-Aspartate Levels in Prefrontal Cortices in Pediatric Bipolar Disorder: A 1H Magnetic Resonance Spectroscopy Study," J Am Acad Child Adolesc Psychiatry 2011, 50(1): 85-94.

Cecil, et al., "Frontal lobe differences in bipolar disorder as determined by proton MR spectroscopy," Bipolar Disord 2002, 4:357-365.

Cerullo, et al., "The functional neuroanatomy of bipolar disorder,". Int Rev Psychiatry 2009; 21:314-22.

Chance, et al., "Multiple controls of oxidative metabolism in living tissues as studied by phosphorus magnetic resonance," Proc Natl Acad Sci USA 1986; 83:9458-62.

Chang, et al., "Decreased N-Acetylaspartate in Children with Familial Bipolar Disorder," Society of Biological Psychiatry 2003, 53:1059-1065.

Chen, et al., "A quantitative meta-analysis of fMRI studies in bipolar disorder," Bipolar Disord 2011, 13:1-15.

Coppen, et al. "Mineral metabolism in mania," Brit Med J 1966; 1:71-5.

Dager, et al., "Research Applications of Magnetic Resonance Spectroscopy (MRS) to Investigate Psychiatric Disorders," Top Magn Reson Imaging 2008, 19(2):81-96.

Deicken, et al., "Abnormal Frontal Lobe Phosphorous Metabolism in Bipolar Disorder," Am J Psychiatry 1995, 152(6):915-918.

Delbello, et al., "Neurochemical predictors of response to pharmacologic treatments for bipolar disorder," Curr Psychiatry Rep 2004; 6:466-72.

Forester, et al., "Brain lithium, N-acetyl aspartate and myo-inositol levels in older adults with bipolar disorder treated with lithium: a lithium-7 and proton magnetic resonance spectroscopy study," Bipolar Disord 2008, 10:691-700.

Freeman, et al., "Energetics of sodium transport in the kidney. Saturation transfer 31P-NMR," Biochimica et Biophysica Acta 1983; 762:325-36.

From, et al., "Regulation of the oxidative phosphorylation rate in the intact cell," Biochemistry 1990; 29:3731-43.

Germana, et al., "The effects of lithium and anticonvulsants on brain structure in bipolar disorder," Acta Psychiatr Scand 2010; 122:481-7.

Glinn, et al., "Inorganic phosphate enhances phosphonucleotide concentrations in cultured fetal rat cortical neurons," Brain Res 1997; 757:85-92.

Goldstein, et al., "Association between sodium- and potassium-activated adenosine triphosphatase alpha isoforms and bipolar disorders," Biol Psychiatry 2009; 65:985-91.

Hallahan, et al., "Structural Magnetic Resonance Imaging in Bipolar Disorder: An International Collaborative Mega-Analysis of Individual Adult Patient Data," Biol Psychiatry 2011, 69:326-335.

Hamakawa, et al., "Reduced Intracellular pH in the basal ganglia and whole brain measured by 31P-MRS in bipolar disorder," Psychiatry and Clinical Neurosciences 2004, 58:82-8.

Iles, et al., "Phosphorylation status of liver by 31P-n.m.r. spectroscopy, and its implications for metabolic control," Biochem J 1985; 229:141-51.

Insel, "Translating Scientific Opportunity Into Public Health Impact," Arch Gen Psychiatry 2009, 66(2):128-133.

Iotti, et al., "Inorganic phosphate is transported into mitochondria in the absence of ATP biosynthesis: an in vivo 31P NMR study in the human skeletal muscle," Biochem Biophys Res Commun 1996; 225:191-4.

Jensen, et al., "Triacetyluridine (TAU) decreases depressive symptoms and increases brain pH in bipolar patients," Exp Clin Psychopharmacol 2008; 16:199-206.

Kato, et al., "Alterations in brain phosphorous metabolism in bipolar disorder detected by in vivo 31P and 7Li magnetic resonance spectroscopy," J Affect Disord 1993; 27:53-60.

Kato, et al., "Brain phosphorous metabolism in depressive disorders detected by phosphorus-31 magnetic resonance spectroscopy," J Affect Disord 1992; 26:223-30.

Kato, et al. "Mitochondrial dysfunction in bipolar disorder," Bipolar Disord 2000, 2:180-190.

Kato, et al., "Lateralized abnormality of high energy phosphate metabolism in the frontal lobes of patients with bipolar disorder detected by phase-encoded 31P-MRS," Psychological Medicine 1995, 25:557-566.

Kato, et al., "Reduction of brain phosphocreatine in bipolar II disorder detected by phosphorous-31 magnetic resonance spectroscopy," J Affective Disorders 1994, 31:125-133.

Kempton, et al., "Meta-analysis, Database, and Meta-regression of 98 Structural Imaging Studies in Bipolar Disorder," Arch Gen Psychiatry 2008, 65(9):1017-1032.

Kirshenbaum, et al., "Decreased neuronal Na(+),K(+)-ATPase activity in Atp1a3 heterozygous mice increases susceptibility to depression-like endophenotypes by chronic variable stress," Genes Brain Behav 2011; 10:542-50.

Kondo, et al., "Open-Label Uridine for Treatment of Depressed Adolescents with Bipolar Disorder," J. Child Adolesc Psychopharmacol 2011, 21(2):171-175.

Looney, et al., "Meta-analysis of erythrocyte Na,K-ATPase activity in bipolar illness," Depress Anxiety 1997; 5:53-65.

Lyoo, et al., "Lithium-induced gray matter volume increase as a neural correlate of treatment response in bipolar disorder: a longitudinal brain imaging study," Neuropsychopharmacology 2010; 35:1743-50.

Marsh, et al., "Neuroimaging studies of normal brain development and their relevance for understanding childhood neuropsychiatric disorders," J Am Acad Child Adolesc Psychiatry 2008; 47:1233-51.

Moore, et al., "Mania, glutamate/glutamine and risperidone in pediatric bipolar disorder: a proton magnetic resonance spectroscopy study of the anterior cingulate cortex," J Affect Disord 2007; 99:19-25.

Mynett-Johnson, et al., "Evidence for an allelic association between bipolar disorder and a Na+, K+ adenosine triphosphatase alpha subunit gene (ATP1A3)," Biol Psychiatry 1998; 44:47-51.

Olvera, et al., "Low levels of N-acetyl aspartate in the left dorsolateral prefrontal cortex of pediatric bipolar patients," J Child Adolesc Psychopharmacol 2007; 17:461-73.

Pan, et al., "Functional neuroimaging studies of bipolar disorder: examining the wide clinical spectrum in the search for disease endophenotypes," Int Rev Psychiatry 2009; 21:368-79.

Patel, et al., "Lithium Treatment Effects on Myo-Inositol in Adolescents with Bipolar Depression," Biol Psychiatry 2006; 60:998-1004.

Patel, et al., "Neurochemical Alterations in Adolescent Bipolar Depression: A Proton Magnetic Resonance Spectroscopy Pilot Study of the Prefrontal Cortex," J Child Adolesc Psychopharmacol 2008; 18(6):623-7.

Patel, et al., "Temporal Change in N-Acetyl-Aspartate Concentrations in Adolescents with Bipolar Depression Treated with Lithium," J Child Adolesc Psychopharmacol 2008; 18(2):132-9.

(56) References Cited

OTHER PUBLICATIONS

Patel, et al., "Open-label lithium for the treatment of adolescents with bipolar depression," J Am Acad Child Adolesc Psychiatry 2006; 45:289-97.

Petroff, et al., "Cerebral intracellular pH by 31P nuclear magnetic resonance spectroscopy" Neurology 1985; 35:781-8.

Phillips, et al., "Medication effects in neuroimaging studies of bipolar disorder," Am J Psychiatry 2008; 165:313-20.

Phillips, et al., "Identifying functional neuroimaging biomarkers of bipolar disorder: toward DSM-V," Schizophr Bull 2007; 33:893-904.

Sassi, et al. "Reduced NAA levels in the dorsolateral prefrontal cortex of young bipolar patients," Am J Psychiatry 2005; 162:2109-15.

Savitz, et al. "Amygdala volume in depressed patients with bipolar disorder assessed using high resolution 3T MRI: the impact of medication," Neuroimage 2010; 49:2966-76.

Stork, et al., "Mitochondrial dysfunction in bipolar disorder: evidence from magnetic resonance spectroscopy research," Mol Psychiatry 2005; 10:900-19.

Vanhamme, et al., "Improved method for accurate and efficient quantification of MRS data with use of prior knowledge," J Magn Reson 1997; 129:35-43.

Wood, et al., "Altered in vitro adaptive responses of lymphocyte Na+,K(+)-ATPase in patients with manic depressive psychosis," J Affect Disord 1991; 21:199-206.

Yildiz, et al., "Lithium-induced alterations in nucleoside triphosphate levels in human brain: a proton-decoupled 31P magnetic resonance spectroscopy study," Psychiatry Res 2005; 138:51-9.

Yildiz, et al., "Nuclear magnetic resonance spectroscopy findings in bipolar illness: a meta-analysis," Psychiatry Res 2001; 106:181-91.

Yoon, et al., "Neurochemical alterations in methamphetamine-dependent patients treated with cytidine-5'-diphosphate choline: a longitudinal proton magnetic resonance spectroscopy study," Neuropsychopharmacology 2010; 35:1165-73.

Yurgelun-Todd, et al., "Functional magnetic resonance imaging studies in bipolar disorder," CNS Spectr 2006; 11:287-97.

Zhang, et al., "Hyperperfusion and cardioplegia effects on myocardial high-energy phosphate distribution and energy expenditure," Am J Physiol 1994; 267:H894-904.

Zhu, et al., "Advanced In Vivo Heteronuclear MRS Approaches for Studying Brain Bioenergetics Driven by Mitochondria," Methods Mol Biol 2009; 489:317-57.

BRAIN PHOSPHORUS SPECTROSCOPY IN BIPOLAR DISORDER

CROSS-REFERENCE TO RELATED APPLICATION

This application claims the benefit of U.S. Provisional Patent Application No. 61/548,176, filed on Oct. 17, 2011, the entirety of which is herein incorporated by reference.

GOVERNMENT LICENSE RIGHTS

This invention was made with government support under Grant R01 MH058681 awarded by National Institutes of Health. The Government has certain rights to this invention.

FIELD

The subject technology generally relates methods of identifying bipolar disorder in humans.

BACKGROUND

Bipolar disorder is a brain disorder that causes extreme shifts in a person's mood, thought, energy, behavior, and ability to function. For many individuals, the onset of bipolar disorder will develop in childhood or adolescence. Unfortunately, the disorder is not always viewed as an illness, and many people suffer for years before an accurate diagnosis is obtained. In some cases, patients with childhood-onset bipolar disorder can experience an average 16.8 year lag between symptom onset and treatment. During that time, patients are often incorrectly diagnosed with major depressive disorder and consequently prescribed psychotropic medication that fails to remedy the bipolar disorder.

Despite the prevalence and severity of bipolar disorder, its neurochemical basis remains obscure. Improvement in diagnosing pediatric bipolar disorder is a critical barrier to progress in the field. One approach in diagnosing pediatric bipolar disorder is to identify neuroimaging biological markers ("biomarkers") that reflect the pathophysiology of bipolar disorder. Without such objective biomarkers, diagnostic accuracy for bipolar disorder remains limited.

SUMMARY

At least one aspect of the disclosure provides methods for identifying bipolar disorder in a person. The methods can include acquiring $^{31}P$ spectroscopic imaging data from a region of interest in a brain of the person. The methods can also include analyzing the $^{31}P$ spectroscopic imaging data to obtain signal intensity and concentration for one or more phosphorus metabolites, wherein a reduced concentration the one or more phosphorus metabolites in the brain of the person is indicative of bipolar disorder in the person. In some embodiments, the person is an unmedicated adolescent, but in other embodiments, the person is an unmedicated adult. In some embodiments, the one or more phosphorus metabolites is inorganic phosphate. In other embodiments, the one or more phosphorus metabolites comprise phophomonoester, phosphodiester, phosphocreatine, and nucleoside triphosphates. In some embodiments, the $^{31}P$ spectroscopic imaging data is obtained using a magnetic resonance imaging system. In some embodiments, acquiring $^{31}P$ spectroscopic imaging data further includes using a two-dimensional magnetic resonance spectroscopy imaging pulse sequence configured to provide phosphorus-31 magnetic resonance spectroscopy. In some embodiments, the concentration for each phosphorus metabolite is calculated as a percentage of a total phosphorus signal acquired from the region of interest. The region of interest can be the frontal lobe of the brain. In some embodiments, the method can also include determining a ratio of concentrations (PCr/Pi) of phosphocreatine (PCr) and Pi, determining, based on the ratio of concentrations, at least one of a likely diagnosis of bipolar disorder or a probability of bipolar disorder in the person.

At least another aspect of the disclosure provides a method for providing an indication of bipolar disorder in an unmedicated person. The method can include measuring a first concentration of inorganic phosphate in a brain of the unmedicated person using in vivo phosphorus-31 magnetic resonance spectroscopy, and measuring a second concentration of inorganic phosphate in a brain of a medicated person or healthy control subject using in vivo phosphorus-31 magnetic resonance spectroscopy. The method can also include comparing the first concentration of inorganic phosphate with the second concentration of inorganic phosphate. In some embodiments, a reduced first concentration of inorganic phosphate compared with the second concentration of inorganic phosphate is indicative of bipolar disorder in the unmedicated person. In some embodiments, the person is an adolescent, but in other embodiments, the person is an adult. In some embodiments, the in vivo phosphorus-31 magnetic resonance spectroscopy is executed using a magnetic resonance imaging system. In some embodiments, the magnetic resonance imaging system is configured to use a two-dimensional magnetic resonance spectroscopy imaging pulse sequence. In some embodiments, the first and second concentrations of inorganic phosphate are measured at a frontal lobe of the brain of the unmedicated person and the medicated person and/or the healthy control subject. The method can further include using the first concentration of inorganic phosphate as a biomarker indicative of bipolar disorder in humans.

At least one aspect of the disclosure includes a non-transitory machine-readable medium encoded with instructions executable by a processing system to perform a method for identifying bipolar disorder in a person. In some embodiments, the instructions include code for acquiring $^{31}P$ spectroscopic imaging data from a region of interest in a brain of the person, by a processor, analyzing the data to obtain a signal intensity and a concentration of inorganic phosphate (Pi), and determining, based on the concentration, at least one of a likely diagnosis of bipolar disorder or a probability of bipolar disorder in the person. Further instructions for the medium can also include determining a ratio of concentrations (PCr/Pi) of phosphocreatine (PCr) and P, and determining, based on the ratio of concentrations, at least one of a likely diagnosis of bipolar disorder or a probability of bipolar disorder in the person. In some embodiments, the concentration is an index concentration, and the determining comprises comparing the index concentration to a threshold concentration obtained from $^{31}P$ spectroscopic data acquired from persons not having bipolar disorder.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses can be combined in any combination, and placed into a respective independent clause, e.g., clause 1 or clause 55. The other clauses can be presented in a similar manner.

1. A method for identifying bipolar disorder in a person, comprising:
   acquiring $^{31}$P spectroscopic data from a region of interest in a brain of the person;
   by a processor, analyzing the data to obtain an indicator of each of a signal intensity and a concentration of inorganic phosphate (Pi); and
   determining, based on the indicators, at least one of a likely diagnosis of bipolar disorder or a probability of bipolar disorder in the person; and
   outputting, by a processor, an indicator of the at least one of the likely diagnosis or the probability.

2. The method of clause 1, further comprising outputting an indicator of a recommendation that a health care worker consider treating the person in view of the at least one of the likely diagnosis or the probability.

3. The method of clause 1, wherein the person is an adolescent.

4. The method of clause 3, wherein the adolescent is unmedicated for a mood disorder.

5. The method of clause 1, wherein the person is unmedicated for a mood disorder.

6. The method of clause 1, wherein the person is an adult.

7. The method of clause 6, wherein the adult is unmedicated for a mood disorder.

8. The method of clause 1, wherein the $^{31}$P spectroscopic data is obtained by magnetic resonance imaging.

9. The method of clause 8, wherein the acquiring $^{31}$P spectroscopic data further comprises using a two-dimensional magnetic resonance spectroscopy imaging pulse sequence configured to provide phosphorus-31 magnetic resonance spectroscopy.

10. The method of clause 1, further comprising:
    determining an indicator of a ratio of concentrations of phosphocreatine (PCr) and Pi; and
    determining, based on the ratio of concentrations, the at least one of a likely diagnosis of bipolar disorder or a probability of bipolar disorder.

11. The method of clause 1, wherein the concentration of inorganic phosphate (Pi) is calculated as a percentage of a total phosphorus signal acquired from the region of interest.

12. The method of clause 1, wherein the concentration is an index concentration, and the determining comprises comparing the index concentration to a threshold concentration obtained from $^{31}$P spectroscopic data acquired from persons not having bipolar disorder.

13. The method of clause 1, wherein the region of interest is the frontal lobe of the brain.

14. A method of treating a person, comprising:
    treating a person, with at least one medication, based on at least one of a likely diagnosis of bipolar disorder or a probability of bipolar disorder in a person;
    wherein the at least one of a likely diagnosis or the probability is derived from the following steps:
      acquiring $^{31}$P spectroscopic data from a region of interest in the brain of the person;
      by a processor, analyzing the data to obtain indicators of a signal intensity and a concentration of inorganic phosphate (Pi);
      determining, based on the indicators of the concentration and the signal intensity, the at least one of the likely diagnosis or the probability.

15. A non-transitory machine-readable medium encoded with instructions executable by a processing system to perform a method for identifying bipolar disorder in a person, the instructions comprising code for:
    acquiring $^{31}$P spectroscopic data from a region of interest in a brain of the person;
    by a processor, analyzing the data to obtain an indicator of each of a signal intensity and a concentration of inorganic phosphate (Pi); and
    determining, based on the indicators, at least one of a likely diagnosis of bipolar disorder or a probability of bipolar disorder in the person; and
    outputting, by a processor, an indicator of the at least one of the likely diagnosis or the probability.

16. The machine-readable medium of clause 15, wherein the instructions further comprise code for outputting an indicator of a recommendation that a health care worker consider treating the person in view of the at least one of the likely diagnosis or the probability.

17. The machine-readable medium of clause 15, wherein the person is an adolescent.

18. The machine-readable medium of clause 17, wherein the adolescent is unmedicated for a mood disorder.

19. The machine-readable medium of clause 15, wherein the person is an adult.

20. The machine-readable medium of clause 19, wherein the adult is unmedicated for a mood disorder.

21. The machine-readable medium of clause 15, further comprising code instructions for:
    determining an indicator of a ratio of concentrations of phosphocreatine (PCr) and Pi; and
    determining, based on the ratio of concentrations, the at least one of a likely diagnosis of bipolar disorder or a probability of bipolar disorder in the person.

22. The machine-readable medium of clause 15, wherein the concentration is an index concentration, and the determining comprises comparing the index concentration to a threshold concentration obtained from $^{31}$P spectroscopic data acquired from persons not having bipolar disorder.

23. A computer-implemented system for identifying bipolar disorder in a person, the system comprising:
    a processing module that processes $^{31}$P spectroscopic data, from a region of interest in a brain of the person, so as to obtain an indicator of each of a signal intensity and a concentration of inorganic phosphate (Pi); and
    an output module, in communication with the processing module, that outputs, based on the indicators, a machine-readable indicator of at least one of a likely diagnosis of bipolar disorder or a probability of bipolar disorder in the person.

24. The system of clause 23, wherein the processing module is further configured to determine a ratio of concentrations of phosphocreatine (PCr) and Pi.

25. The system of clause 24, wherein the output module is further configured to output, based on the ratio of concentrations, another machine-readable indicator of at least one of a likely diagnosis of bipolar disorder or a probability of bipolar disorder in the person.

26. The system of clause 23, wherein the person is an adolescent.

27. The system of clause 26, wherein the adolescent is unmedicated for a mood disorder.

28. The system of clause 23, wherein the person is unmedicated for a mood disorder.

29. The system of clause 23, wherein the person is an adult.

30. The system of clause 29, wherein the adult is unmedicated for a mood disorder.

31. The system of clause 23, wherein the $^{31}$P spectroscopic imaging data is obtained by magnetic resonance imaging.

Additional features and advantages of the subject technology will be set forth in the description below, and in part will be apparent from the description, or can be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology. Unless otherwise defined, all technical and scientific terms used herein have the same meaning as commonly understood by one of ordinary skill in the art to which the subject technology belongs. Although suitable methods and materials for the practice of the subject technology are described below, other methods and materials similar or equivalent to those described herein, which are well known in the art, can also be used. All publications, patent applications, patents, and other references mentioned herein are incorporated by reference in their entirety. In case of conflict, the present specification, including definitions, will control. In addition, the materials, methods, and examples are illustrative only and not intended to be limiting.

BRIEF DESCRIPTION OF THE DRAWINGS

The accompanying drawings, which are included to provide further understanding of the subject technology and are incorporated in and constitute a part of this specification, illustrate aspects of the disclosure and together with the description serve to explain the principles of the subject technology.

DETAILED DESCRIPTION

In the following detailed description, numerous specific details are set forth to provide a full understanding of the subject technology. It will be apparent, however, to one ordinarily skilled in the art that the subject technology can be practiced without some of these specific details. In other instances, well-known structures and techniques have not been shown in detail so as not to obscure the subject technology.

Recent studies have implicated mitochondrial dysfunction in the living human brain with the pathophysiology of bipolar disorder, see, e.g., Kato et al., *Mitochondrial Dysfunction in Bipolar Disorder*, BIPOLAR DISORDER, 2000, 2:180-90, the contents of which are incorporated by reference. Other studies utilizing neuroimaging via magnetic resonance spectroscopy (MRS) have also provided an internally consistent body of evidence for mitochondrial involvement in bipolar disorder, see, e.g., P. Renshaw & C. Stork, *Mitochondrial Dysfunction in Bipolar Disorder: Evidence from Magnetic Resonance Spectroscopy Research*, MOLECULAR PSYCHIATRY, 2005, 10:900-19 the contents of which are incorporated by reference.

Magnetic resonance spectroscopy allows in vivo analysis of the neurochemical alterations associated with psychiatric disorders. To evaluate particular neurochemical alterations, MRS equipment can be adapted to retrieve and report signals for specific chemical nuclei or metabolites (i.e., neurometabolites) found within the human brain. The presence of such chemical nuclei and/or metabolites may provide researchers or doctors with neuroimaging biomarkers that indicate the general biological state of the brain. Consequently, an accurate, or at least more accurate, diagnosis of the particular psychiatric disorder can be had based on objective findings.

In some applications, phosphorus metabolites may be considered as neuroimaging biomarkers that may be measured and evaluated to determine the biological state of the brain. For example, the concentration (or lack thereof) of phosphorus metabolites reflects mitochondrial function or dysfunction in the brain, which can be considered an indicator in various psychiatric disorders, such as bipolar disorder. Such phosphorus metabolites include, but are not limited to, phosphocreatine (PCr), inorganic phosphate (Pi), and betanucleoside triphosphate (β-NTP) (i.e., largely adenosine triphosphate, or ATP), and can be measured using phosphorus-31 magnetic resonance spectroscopy ($^{31}$P-MRS). Phosphorus-31 magnetic resonance spectroscopy is capable of non-invasive measurement of phosphorus metabolites reflecting mitochondrial function in the living human brain.

Figure 1:
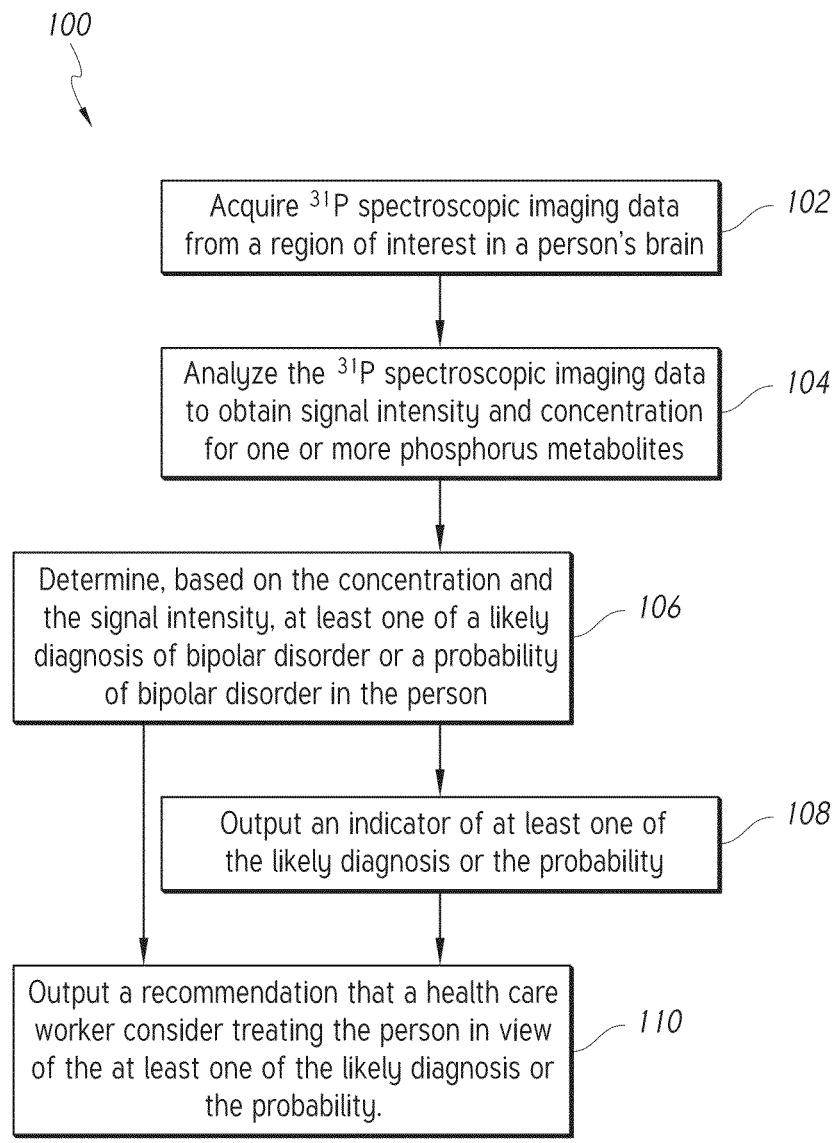
FIG. 1 illustrates a method for identifying bipolar disorder in a person, according to one or more embodiments.

FIG. 1 illustrates a method 100 for identifying bipolar disorder in a person, according to one or more embodiments. In some embodiments, the person can be an unmedicated adolescent. In other embodiments, the person is an unmedicated adult. As used herein, the term "adolescent" may refer to an individual that is less than twenty years old, and typically 13 to 19 years old. On the other hand, the term "adult" may refer to an individual that is older than an adolescent, as defined.

Moreover, as used herein, the term "unmedicated" refers, in some embodiments, to the absence of pharmacological treatments for bipolar disorder, such as mood stabilizers like lithium and valproic acid or other psychotropic medications used to treat bipolar disorder. Accurate neuroimaging of biomarkers can be confounded through the use of psychotropic medication which affects the brain regions of interest. In contrast, neuroimaging of unmedicated persons (e.g., bipolar disorder patients) allow researchers to identify biomarkers of both bipolar illness and treatment response, without confounding by current treatment.

The method 100 can include acquiring $^{31}$P spectroscopic imaging data from a region of interest in the person's brain, as at 102. In some embodiments, the region of interest in the brain is the frontal lobe. In other embodiments, the region of interest can be other parts of the brain. In some embodiments, the region of interest can be the entire brain. The $^{31}$P spectroscopic imaging data can be acquired using, for example, a magnetic resonance imaging system (MRI), such as a Siemens Trio 3 Tesla whole body MRI system available from Siemens Medical Solutions located in Erlangen, Germany. The MRI system can further be equipped with a $^{31}$P/$^{1}$H double-tuned volume head coil. In some embodiments, the $^{31}$P spectroscopic imaging data are obtained using a two-dimensional magnetic resonance spectroscopy imaging pulse sequence (2D magnetic resonance spectroscopic imaging) configured to provide phosphorus-31 magnetic resonance spectroscopy.

The method 100 can include analyzing the $^{31}$P spectroscopic imaging data to obtain signal intensity and concentration, or an indicator of signal intensity and an indicator of concentration, for one or more phosphorus metabolites, as at 104. The one or more phosphorus metabolites that can be measured include, but are not limited to, phophomonoester (PME), inorganic phosphate (Pi), phosphodiester (PDE), phosphocreatine (PCr), and nucleoside triphosphates (e.g., γ-NTP, α-NTP, and β-NTP). In one or more embodiments, concentrations for each phosphorus metabolite are calculated as a percentage of a total phosphorus signal acquired from the region of interest. The concentration can thus be a relative concentration. In embodiments where a reduced concentration of Pi in the brain is determined as compared to healthy controls and/or medicated persons having bipolar disorder, this can be indicative of bipolar disorder, or a propensity for such an illness, in the person. The method 100 can comprise determining, based on the concentration and the signal intensity, at least one of a likely diagnosis of bipolar disorder or a probability of bipolar disorder in the person, as at 106.

The method 100 can comprise outputting an indicator of the at least one of the likely diagnosis or the probability, as at 108. Additionally or alternatively, the method 100 can comprise outputting a recommendation, or a indicator of a recommendation, that a health care worker consider treating the person in view of the at least one of the likely diagnosis or the probability, as at 110.

Figure 2:
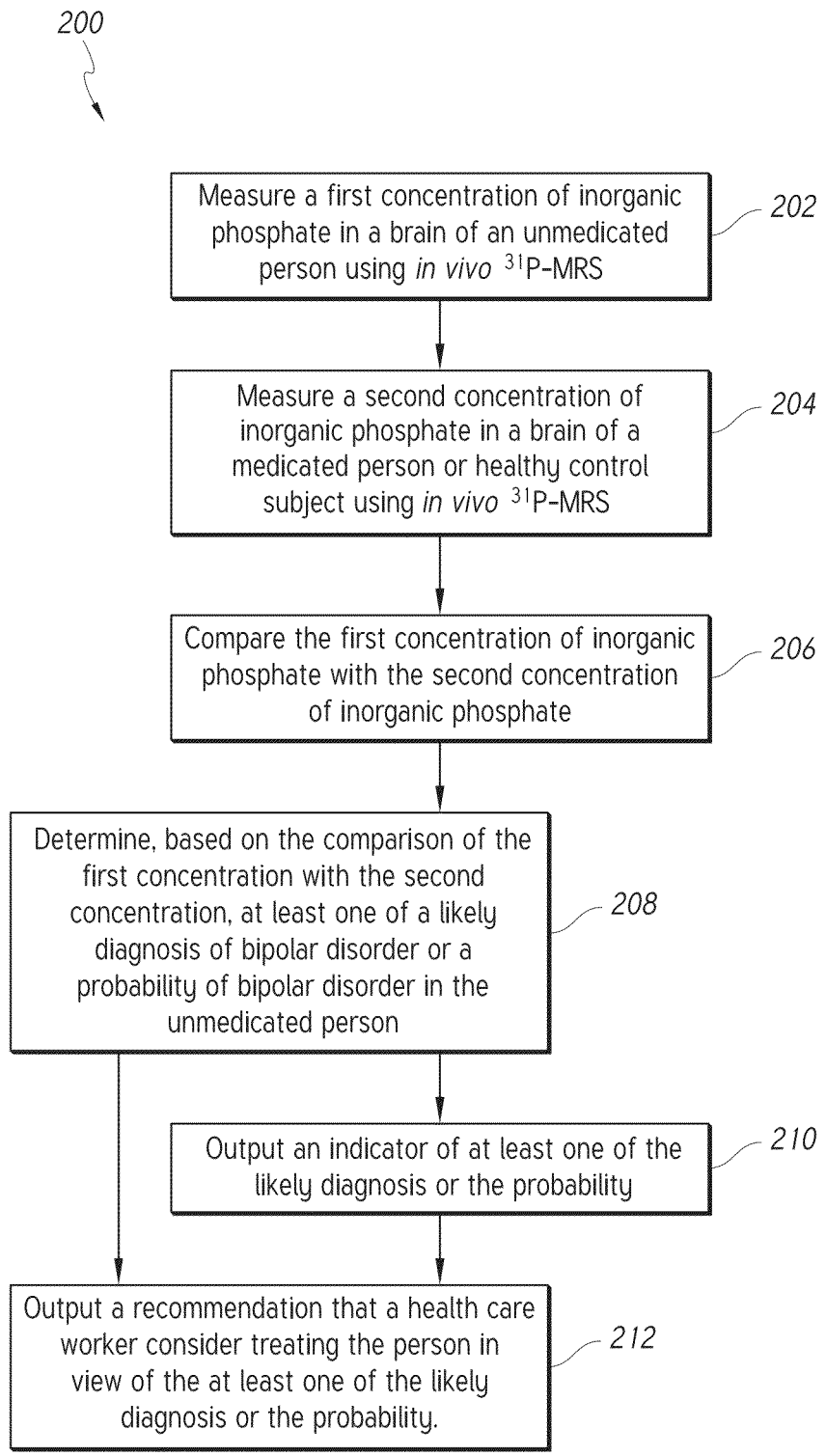
FIG. 2 illustrates a method for providing an indication of bipolar disorder in an unmedicated person, according to one or more embodiments.

Referring now to FIG. 2, illustrated is a method 200 for providing an indication of bipolar disorder in an unmedicated person, according to one or more embodiments. As with the method 100 discussed above, the person can be an adolescent or an adult, and the term "unmedicated" refers to the absence of pharmacological treatments for bipolar disorder. The method 200 can include measuring a first concentration of inorganic phosphate in a brain of the unmedicated person using in vivo phosphorus-31 magnetic resonance spectroscopy ($^{31}$P-MRS), as at 202. In one embodiment, the in vivo $^{31}$P-MRS can be executed using a magnetic resonance imaging system. In other embodiments, the in vivo $^{31}$P-MRS can be executed using any other machine or device configured to measure or otherwise indicate a concentration of inorganic phosphate metabolites in the brain. In some embodiments, the magnetic resonance imaging system can be configured to use a two-dimensional magnetic resonance spectroscopy imaging pulse sequence in order to provide the in vivo $^{31}$P-MRS.

The method 200 can include measuring a second concentration of inorganic phosphate in a brain of a medicated person or healthy control subject using in vivo $^{31}$P-MRS, as at 204. In some embodiments, the medicated person is a person that has been previously-diagnosed with bipolar disorder and currently undertaking pharmacological treatments for the illness. In some embodiments, the healthy control subject can be a person that does not have bipolar disorder and has an absence of Axis I psychiatric or substance use disorders. In some embodiments, the medicated person and/or healthy control subject can be an adolescent. In other embodiments, the medicated person and/or healthy control subject can be an adult. In some embodiments, the first and second concentrations of inorganic phosphate are measured at a frontal lobe of the brain of the unmedicated person and the medicated person and/or the healthy control subject.

The method 200 can further include comparing the first concentration of inorganic phosphate with the second concentration of inorganic phosphate, as at 206. In one or more embodiments, a reduced first concentration of inorganic phosphate as compared with the second concentration of inorganic phosphate can be an indication of bipolar disorder in the unmedicated person. The method 200 can comprise determining, based on the comparison of the first concentration with the second concentration, at least one of a likely diagnosis of bipolar disorder or a probability of bipolar disorder in the unmedicated person, as at 208.

The method 200 can comprise outputting an indicator of the at least one of the likely diagnosis or the probability, as at 210. Additionally or alternatively, the method 200 can comprise outputting a recommendation, or an indicator of a recommendation, that a health care worker consider treating the person in view of the at least one of the likely diagnosis or the probability, as at 212.

Accordingly, frontal lobe inorganic phosphate concentration in medication-free adolescents with bipolar depression can provide a biomarker for the illness. This conclusion was reached by Applicants by comparing the concentrations of phosphorus metabolites associated with mitochondrial function in the frontal lobe of depressed adolescents with bipolar disorder and healthy control subjects. The following example provides details of the study undertaken by Applicants.

EXAMPLE

The concentrations of high-energy phosphorus metabolites associated with mitochondrial function in the frontal lobe of depressed adolescents with bipolar disorder and healthy controls were compared. In vivo phosphorus-31 magnetic resonance spectroscopy ($^{31}$P-MRS) was performed at 3 Tesla to measure phosphocreatine (PCr), beta-nucleoside triphosphate (β-NTP), inorganic phosphate (Pi) and other neurometabolites in the frontal lobe of 14 adolescents with bipolar disorder and 24 adolescent healthy controls. Of the 14 adolescents with bipolar disorder, 8 were medication-free and 6 were medicated.

Figure 4A:
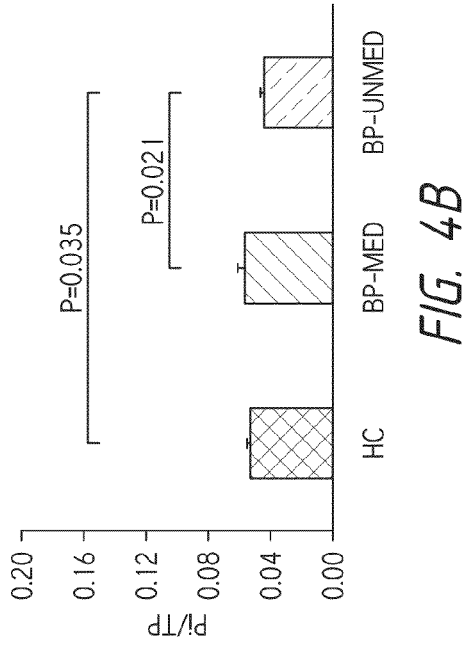
FIG. 4A illustrates a bar graph depicting frontal lobe phosphorus metabolite levels and Post-hoc Tukey-Kramer pairwise comparisons, according to one or more embodiments.
Figure 4B:
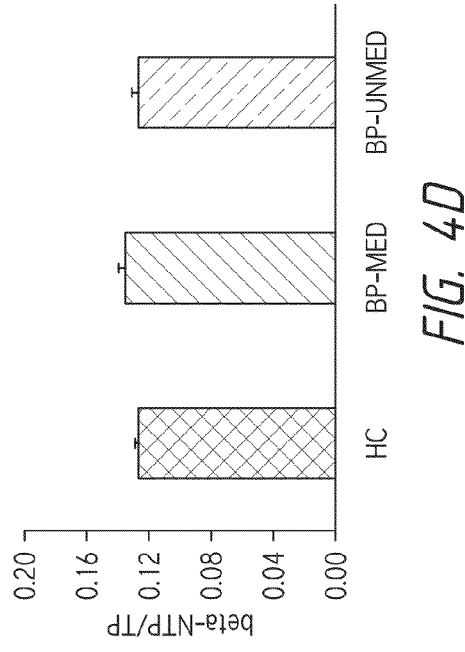
FIG. 4B illustrates a bar graph depicting frontal lobe phosphorus metabolite levels and Post-hoc Tukey-Kramer pairwise comparisons, according to one or more embodiments.
Figure 4C:
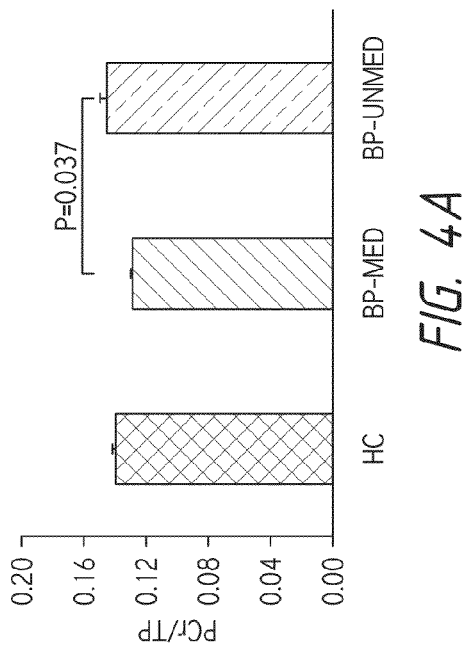
FIG. 4C illustrates a bar graph depicting frontal lobe phosphorus metabolite levels and Post-hoc Tukey-Kramer pairwise comparisons, according to one or more embodiments.
Figure 4D:
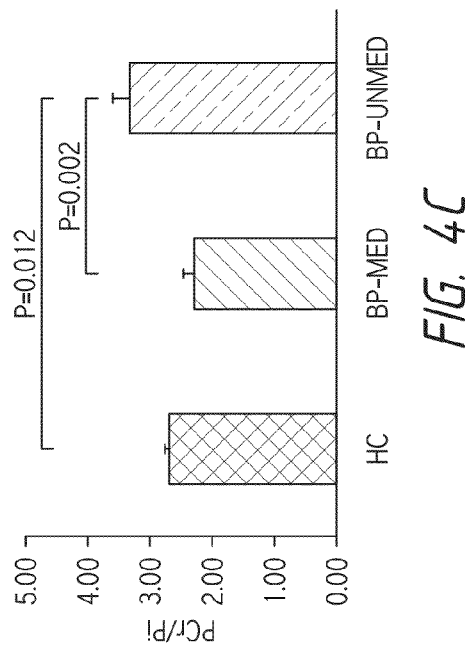
FIG. 4D illustrates a bar graph depicting frontal lobe phosphorus metabolite levels, according to one or more embodiments.

A one-way analysis of variance between groups revealed differences in PCr (p=0.039), Pi (p=0.015) and PCr/Pi (p=0.002) between the participant groups. For example, post-hoc Tukey-Kramer analysis showed that the unmedicated bipolar disorder participants had decreased Pi compared with both healthy control (17%; p=0.035) and medicated bipolar disorder (22%; p=0.021) participants, as illustrated in FIG. 4B. Moreover, the unmedicated bipolar disorder group had increased PCr compared with medicated bipolar disorder (11%; p=0.037), as illustrated in FIG. 4A. The PCr/Pi ratio was increased in unmedicated bipolar disorder compared with healthy control (24%; p=0.012) and medicated bipolar disorder (p=0.002) participants, as illustrated in FIG. 4C. No differences in β-NTP, as illustrated in FIG. 4D, or pH were observed. These results support the view that frontal lobe mitochondrial function is altered in adolescent bipolar disorder patients, and may have implications for the use of Pi as a biomarker. These findings join volumetric studies of the amygdala, and proton MRS studies of n-acetyl aspartate (NAA), in pointing to potential differences in neurobiology between pediatric and adult bipolar disorder.

Among adults with bipolar disorder, up to 65% report the age-of-onset in childhood or adolescence. In persons 10 to 24 years of age, who make up 27% of the world's population, bipolar disorder is the 4th leading cause of disability. Patients with bipolar disorder experience long delays to diagnosis and appropriate treatment. In fact, patients with childhood-onset bipolar disorder experience a lag between symptom onset and treatment averaging 16.8 years. Despite bipolar disorder's prevalence and severity, and the health care system's inability to identify cases in a timely fashion, its neurochemical basis remains obscure. Improvement in diagnosing pediatric bipolar disorder is a critical barrier to progress in the field. One approach advocated by both the NIMH Strategic Plan and the Research Agenda for DSM-V, is to identify neuroimaging biomarkers that reflect bipolar disorder's pathophysiology.

Converging lines of evidence implicate mitochondrial dysfunction in the pathophysiology of bipolar disorder, including molecular, family-based, expression analysis, proteomic, in vitro, cerebrospinal fluid, post-mortem, and animal studies. Moreover, studies of bipolar disorder utilizing the neuroimaging method magnetic resonance spectroscopy (MRS) provide an internally consistent body of evidence for mitochondrial involvement in bipolar disorder.

Magnetic resonance spectroscopy is a method that allows in vivo analysis of the neurochemical alterations associated with psychiatric disorders. Phosphorus MRS ($^{31}$P-MRS) is a method capable of noninvasive measurement of the phosphorus metabolites reflecting mitochondrial function in living human brain. However, other methods of noninvasive measurement of the phosphorus metabolites, such as those developed in the future, for example, may be used. These phosphorus metabolites include phosphocreatine (PCr), inorganic phosphate (Pi), and betanucleoside triphosphate ($\beta$-NTP) (largely adenosine triphosphate, or ATP).

Psychotropic medication affects the brain regions of interest (ROI) to neuroimaging researchers. The effects of medication class, duration of drug exposure, and polypharmacy have yet to be elucidated. Moreover, neurochemical alterations in psychiatric disorders could result from medication effects, disease processes, or both. In pediatric populations, the interaction between the brain and medication is further complicated by neurodevelopment. These confounds make it difficult to interpret cross-sectional neuroimaging data acquired from medicated bipolar disorder patients.

In contrast, neuroimaging of medication-free bipolar disorder patients provides investigators with the opportunity to identify biomarkers of both bipolar illness and treatment response, without confounding by current treatment. In fact, inclusion of medicated participants in cross-sectional bipolar disorder neuroimaging studies is considered a major methodological weakness. Notwithstanding this, expert recommendations for cross-sectional studies of bipolar disorder include comparison of neuroimaging findings in medicated vs. unmedicated individuals.

Studies of adults with bipolar disorder have used $^{31}$P-MRS to compare high-energy phosphate concentrations in bipolar disorder patients and healthy controls, but to Applicants' knowledge this method has not been applied to study adolescent bipolar disorder. Accordingly, it is hypothesized that medication-free adolescents with bipolar depression would demonstrate lower concentrations of cerebral PCr compared with healthy controls, in parallel with findings in adults. Published studies of pediatric bipolar disorder using an alternative method, proton MRS ($^{1}$H-MRS), have focused on the frontal lobe for chemical analysis. Accordingly, Applicants selected a frontal lobe ROI to interrogate with $^{31}$P-MRS.

The bipolar disorder participants were recruited to participate in a clinical trial. Consecutive adolescents who met inclusion criteria were enrolled in the clinical trial. Inclusion criteria for bipolar disorder participants were: outpatient status; male or female 13-18 years of age; a primary diagnosis of Bipolar Disorder I, II or NOS; current major depressive episode of greater than 2 weeks duration with a Children's Depression Rating Scale-Revised (CDRS-R) raw score of greater than 40. Participants could be medication-free; for those taking medication, Applicants required their regimen to be stable for greater than 2 weeks.

Exclusion criteria for participants with bipolar disorder were: clinically significant abnormality on complete blood count, comprehensive metabolic profile, thyroid stimulating hormone or urinalysis; psychotic symptoms; high risk for suicidal behavior; primary Axis I diagnosis other than bipolar disorder; Young Mania Rating Scale (YMRS) score greater than 10; mental retardation; contraindication to magnetic resonance imaging (e.g. ferromagnetic implant or claustrophobic anxiety); and positive urine drug screen.

Inclusion criteria for healthy control participants were: male or female 13-18 years of age; and absence of an Axis I psychiatric or substance use disorder. Exclusion criteria for healthy control participants were: clinically significant neurological or medical condition; contraindication to magnetic resonance imaging; and positive urine drug screen. Pregnant females and nursing mothers were excluded from participation in either the bipolar disorder or healthy control group. Diagnoses were established with the Schedule for Affective Disorders and Schizophrenia for School-Age Children-Present and Lifetime Version (K-SADS-PL) administered by a board-certified child and adolescent psychiatrist. All participants underwent identical psychiatric evaluations prior to $^{31}$P-MRS neuroimaging.

Phosphorus Spectroscopic Neuroimaging.

Neuroimaging data were acquired using a Siemens Trio 3 Tesla whole body MRI system (Siemens Medical Solutions, Erlangen, Germany) with Avanto gradients (45 mT/m strength and 150 T/m/s slew rate) and a $^{31}$P/$^{1}$H double-tuned volume head coil (Clinical MR Solutions, LLC, Brookfield, Wis.). $^{31}$P spectroscopic imaging data were acquired using a two-dimensional magnetic resonance spectroscopy imaging pulse sequence (2D MRSI) with the following parameters: Field of View (FOV) 20×20×2.5 cm3; Receiver bandwidth=2.5 kHz; TR/TE=3000/2.3 ms; Flip angle=900; Average number=24; Vector size=1024; Matrix size=8×8; and Voxel dimension=2.5×2.5×2.5 cm3.

To facilitate voxel placement, high resolution T1 weighted images were acquired using a three-dimensional magnetization-prepared rapid gradient echo acquisition (MPRAGE) pulse sequence with the following parameters: TR/TE/TI=2000/3.37/1100 ms; Flip angle=80; Field of view=25651925144 mm3; 25651925144 matrix size; 1×1×1 mm3 spatial resolution; Bandwidth=300 Hz/pixel. To effectively saturate unnecessary fat signal from the scalp, six outer volume saturation bands were placed in the scalp and skull regions.

Figure 3:
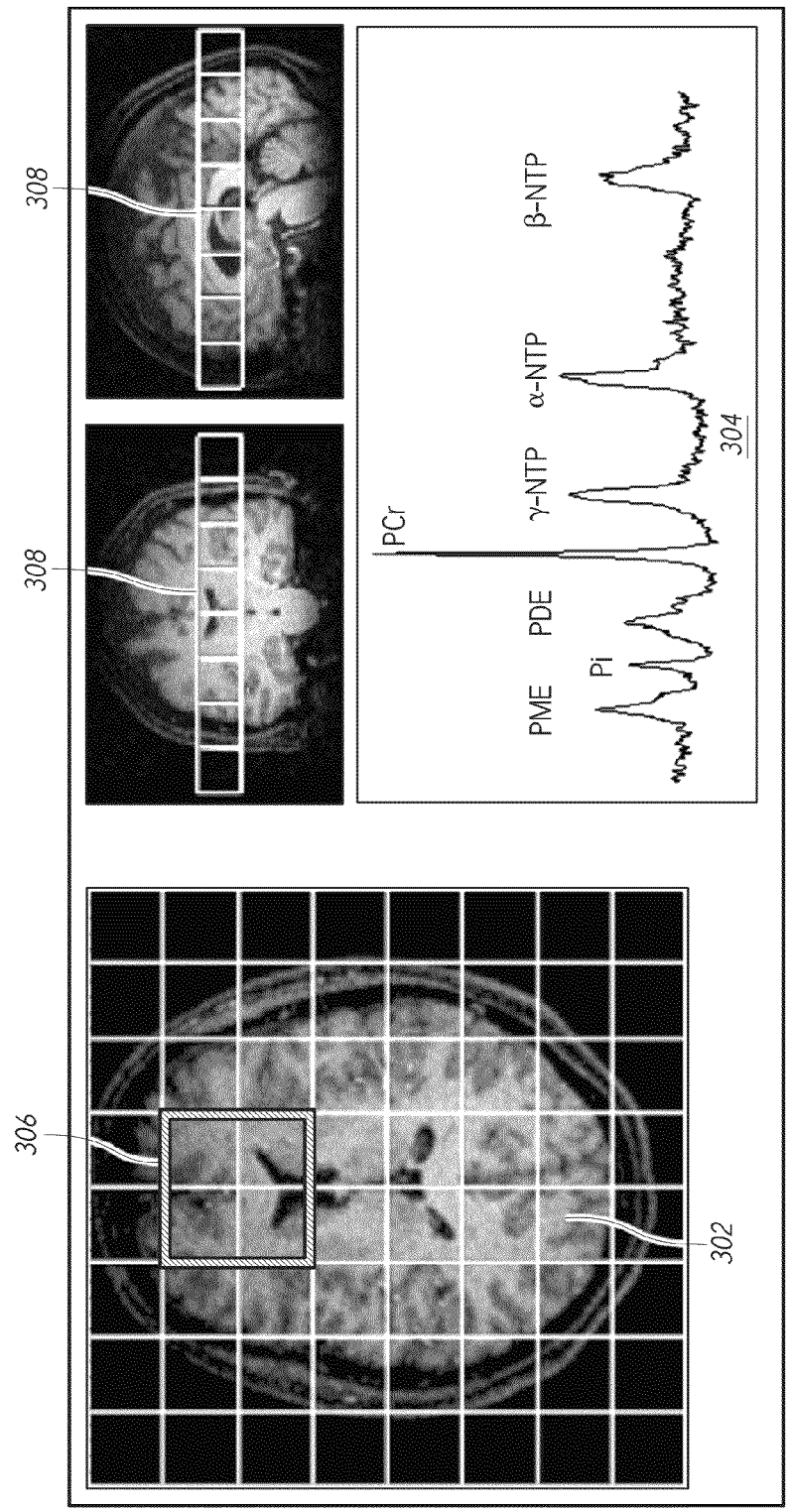
FIG. 3 illustrates a region of interest in a human brain and further displays a representative $^{31}$P-MRS spectrum, according to one or more embodiments disclosed.

FIG. 3 depicts the region of interest in the brain 302, and displays a representative $^{31}$P-MRS spectrum 304. As shown in FIG. 3, the region of interest for acquiring the data was the frontal lobe of the human brain. Specifically, the top/left image depicts the voxel placement 306 at the frontal lobe, and the top/right image illustrates the axial slice 308 location. As an output, the $^{31}$P-MRS spectrum 304 is displayed to indicate the various phosphate metabolites being measured. The anterior-posterior (AC-PC) line was identified on the midsagittal images acquired by MPRAGE pulse sequence. The 2D MRSI grid was placed immediately above the plane formed by the anterior-posterior commissure (AC-PC) line and covers anterior cingulate cortex, corpus callosum and occipital lobe. Board-certified radiologists reviewed the anatomic images to rule out the presence of intracranial abnormalities.

Phosphorus Metabolite Data Analysis

All $^{31}$P spectra were preprocessed using a MATLAB-based application (The MathWorks, Inc., Natick, Mass.). Each spectrum was apodized with 10 Hz Lorentzian line broadening before zerofilling and Fast Fourier Transform. The zero-order and first-order phase corrections were performed in all spectra. The signal intensity of each metabolite was obtained using the Advanced Method for Accurate, Robust and Efficient Spectral Fitting of MRS data with use of prior knowledge (AMARES) fitting algorithm within the software application jMRUI 4.0. Metabolite concentrations were calculated as a percentage of the total phosphorus (TP) signal acquired from the region of interest. Intracellular pH was calculated according to the method of Petroff et al., as described in A. Petroff et al., *Cerebral Intracellular pH by $^{31}$P Nuclear Magnetic Resonance Spectroscopy*, NEUROLOGY 1985, 35:781-8.

Statistical Analysis

Statistical analyses were performed using JMP 9.0.2 (SAS Institute Inc., Cary, N.C.). Levene's test was used to confirm the homogeneity of variances between groups. The goodness of fit of the metabolite distributions was assessed with the Shapiro-Wilk test. The a priori hypotheses were tested with one-way analysis of variance for continuous variables and the $\chi^2$ test for categorical variables, respectively. Covariation with age was not required. Due to the limited sample size, gender effects were not considered. Group assignment, whether medicated bipolar disorder, unmedicated bipolar disorder, or healthy control, was the independent variable, with metabolite concentrations in the frontal lobe region of interest serving as dependent variables. Post-hoc analyses were conducted using the Tukey-Kramer Honestly Significant Difference test, which simultaneously compares all possible pairwise differences between group means.

Results $^{31}$P-MRS scans of the 14 depressed adolescents with bipolar disorder and the 24 healthy controls were acquired. No intracranial abnormalities were detected on participants' anatomical MRIs. Demographic data for the unmedicated bipolar disorder, medicated bipolar disorder, and healthy control participants are presented in Table 1 below, where SD is "standard deviation," and CDRS-R is "Children's Depression Rating Scale-Revised."

TABLE 1

|  | Unmedicated BD (n = 8) | Medicated BD (n = 6) | Healthy Control (n = 24) | p-value* |
|---|---|---|---|---|
| Mean Age, Years ± SD | 15.6 ± 1.0 | 15.5 ± 0.8 | 15.7 ± 1.7 | 0.99* |
| Female Gender | 5 | 2 | 11 | — |
| CDRS-R Raw Score ± SD | 60.4 ± 11.0 | 55.7 ± 13.9 | 20.8 ± 3.9 | <0.01* |
| Medication Naïve (percent) | 4 (50%) | 0 (0%) | 24 (100%) | — |
| Mean Duration Unmedicated ± SD** | 70 ± 47.5 weeks | N/A | N/A | — |

*One-way ANOVA
**Four of eight unmedicated BD participants had prior exposure to psychotropic medication There were no significant between-group differences between bipolar disorder participants and healthy control participants in age, educational level or handedness. The participants' history of exposure to psychotropic medication is presented in Table 2.

TABLE 2

| Age, years; Gender | Medicated? | Medication(s) and (Duration Prior to Brain Scan) | Medication Naïve? | Medication-Free Period Prior to Study | Comment |
|---|---|---|---|---|---|
| 15, female | No | N/A | No | 28 weeks | Prior drug: quetiapine. |
| 17, female | No | N/A | Yes | N/A | Medication naïve. |
| 15, female | No | N/A | No | 106 weeks | Prior drug: citalopram. |
| 16, male | No | N/A | Yes | N/A | Medication naïve. |
| 17, female | No | N/A | No | 30 weeks | Prior drug: divalproex sodium. |
| 13, male | No | N/A | Yes | N/A | Medication naïve. |
| 17, male | Yes | Aripiprazole 10 mg; Trazodone 100 mg (68 weeks) | No | N/A | Medicated during study. |
| 16, male | Yes | Methylphenidate 36 mg; Melatonin 3 mg (92 weeks) | No | N/A | Medicated during study. |
| 15, female | No | N/A | No | 116 weeks | Prior drug: sertraline. |
| 17, male | Yes | Lamotrigine 200 mg; Citalopram 10 mg (150 weeks) | No | N/A | Medicated during study. |
| 18, female | Yes | Bupropion 150 mg (8 weeks) | No | N/A | Medicated during study. |
| 17, male | Yes | S-Adenosyl Methionine 200 mg (2 weeks) | No | N/A | Medicated during study. |

TABLE 2-continued

| Age, years; Gender | Medicated? | Medication(s) and (Duration Prior to Brain Scan) | Medication Naïve? | Medication-Free Period Prior to Study | Comment |
|---|---|---|---|---|---|
| 17, female | Yes | Escitalopram 40 mg; Dexmethylphenidate 20 mg; Topiramate 50 mg (130 weeks) | No | N/A | Medicated during study. |
| 17, male | No | N/A | Yes | N/A | Medication naïve. |

In the unmedicated bipolar disorder group, four participants were medication-naïve. The four remaining unmedicated bipolar disorder participants had a mean medication-free period prior to entering the study of 70+47.5 weeks (range, 28-116 weeks). Table 3 displays one-way analysis of variance results comparing $^{31}$P-MRS results across the three participant groups. Group differences were found in PCr (F (2, 35)=3.555; p=0.039), Pi (F (2, 35)=4.733; p=0.015) and PCr/Pi (F (2, 35)=7.351; p=0.002). There were no significant differences in frontal lobe β-NTP concentration (F (2, 35)=0.799; p=0.458), or pH (F (2, 35)=0.249; p=0.781).

TABLE 3

| Frontal Lobe Metabolite * | Unmedicated BD (n = 8) | Medicated BD (n = 6) | Healthy Control (n = 24) | ANOVA F(2, 35) | p-value |
|---|---|---|---|---|---|
| PCr (SD) | 0.145 (0.013) | 0.129 (0.003) | 0.140 (0.012) | 3.555 | 0.039 |
| Pi (SD) | 0.045 (0.007) | 0.058 (0.009) | 0.054 (0.008) | 4.733 | 0.015 |
| PCr/Pi (SD) | 3.321 (0.772) | 2.281 (0.395) | 2.668 (0.455) | 7.351 | 0.002 |
| β-NTP (SD) | 0.127 (0.013) | 0.135 (0.013) | 0.127 (0.015) | 0.799 | 0.458 |
| PCr/β-NTP (SD) | 1.153 (0.198) | 0.961 (0.098) | 1.127 (0.188) | 2.395 | 0.106 |
| pH (SD) | 7.062 (0.042) | 7.050 (0.022) | 7.053 (0.034) | 0.249 | 0.781 |
| PME (SD) | 0.139 (0.028) | 0.134 (0.016) | 0.135 (0.015) | 0.157 | 0.856 |
| PDE (SD) | 0.183 (0.019) | 0.194 (0.015) | 0.183 (0.021) | 0.841 | 0.440 |
| Mg$^{2+}$ (μmol/L)(SD) | 0.209 (0.083) | 0.165 (0.021) | 0.248 (0.200) | 0.663 | 0.522 |

* The total phosphorus concentration peak was used for standardization

Post-hoc Tukey-Kramer HSD pair-wise comparisons are shown in FIG. 4 in the form of bar graphs a)-d). Applicants found increased PCr in unmedicated bipolar disorder participants compared with medicated bipolar disorder (p=0.037). Mean PCr in the healthy controls was not significantly different from medicated bipolar disorder (p=0.078). Unmedicated bipolar disorder participants demonstrated decreased Pi compared to both healthy controls (p=0.035) and medicated bipolar disorder participants (p=0.021). The PCr/Pi ratio was increased in unmedicated bipolar disorder compared with HC (p=0.012).

Discussion

To the knowledge of Applicants, this was the first $^{31}$P-MRS study of pediatric bipolar disorder. The a priori hypothesis that frontal lobe PCr would be reduced in depressed adolescents with bipolar disorder was not confirmed in this study. This result could be due to a lack of statistical power associated with the sample size, a limitation recognized as pervasive in neuroimaging studies of bipolar disorder. In the search for neuroimaging biomarkers of bipolar disorder, it is useful to compare healthy controls with medication-free participants because of the established effects of medication on brain chemistry and brain structure. Another potential explanation for the results is that adolescent bipolar disorder and adult bipolar disorder display dissimilar neurochemical characteristics. For example, lithium administration decreases prefrontal N-acetylaspartate (NAA) levels in adolescent bipolar disorder, but increases NAA concentrations in the prefrontal cortex of lithium-treated bipolar disorder adults. Adding to the support for neurobiological differences between pediatric and adult bipolar disorder are the studies documenting decreased amygdala volume in pediatric bipolar disorder, and contrapositive results in adults with bipolar disorder.

At least one unexpected result or finding obtained from the study was the reduced Pi in the medication-free bipolar disorder participants, in whom Pi was decreased compared to the healthy controls (17%; p=0.035) and medicated bipolar disorder (22%; p=0.021) participants. This provides an apparent relation between a finding of decreased concentration of Pi and the 'mitochondrial hypothesis' of bipolar disorder. This may be explained by the fact that at least three independent research groups have concluded that oxidative phosphorylation, the ubiquitous metabolic pathway for ATP production, is principally controlled by Pi. Furthermore, it is thought that the only Pi that is detectable by nuclear magnetic resonance is involved in oxidative phosphorylation. Mammalian cells in which oxidative phosphorylation is impaired can reduce the concentration of free Pi, via compartmentation to the inner mitochondrial membrane, which immobilizes the phosphorus ions and renders them 'invisible' to MRS. In addition, Pi has a direct effect in vitro on glucose utilization in cortical neurons. It has been posited that decreased ATP consumption leads to a fall in cytosolic Pi, to a level that balances ATP synthesis and utilization, thus stabilizing the cell's phosphorylation potential.

Additional support for the relevance of Pi to the pathophysiology of bipolar disorder is provided by the enduring observation that the activity of sodium-potassium adenosine triphosphatase (Na+/K+-ATPase), an enzyme partially regulated by Pi, is altered in patients with bipolar disorder. In addition, there is a genetic association between bipolar disorder and mutations in Na+/K+-ATPase. The normal response of lymphocyte Na+/K+-ATPase to incubation with lithium is absent in the lymphocytes of bipolar disorder patients, regardless of their medication status. In animal models, decreased neuronal Na+/K+-ATPase activity increases susceptibility to chronic variable stress depression paradigms.

Sodium-potassium adenosine triphosphatase is the receptor for digitalis-like compounds (DLC), which are implicated in mood regulation. Furthermore, binding for DLC in bipolar disorder is separable from that observed in both major depressive disorder and schizophrenia. Neutralization of DLC alters catecholamine metabolism in Sprague-Dawley rats: ventral tegmental area dopamine levels rise 55%, and the hippocampal norepinephrine/dopamine ratio increases more than fifteen-fold. Finally, blocking DLC elicits an antidepressant-like response in the Flinders Sensitive Line of genetically depressed rats.

Modification of each of the above-described methods for carrying out the subject technology, and variations of aspects of the disclosure that are apparent to those of skill in the art are intended to be within the scope of the claims. Furthermore, no element, component or method step is intended to be dedicated to the public regardless of whether the element, component or method step is explicitly recited in the claims.

Figure 5:
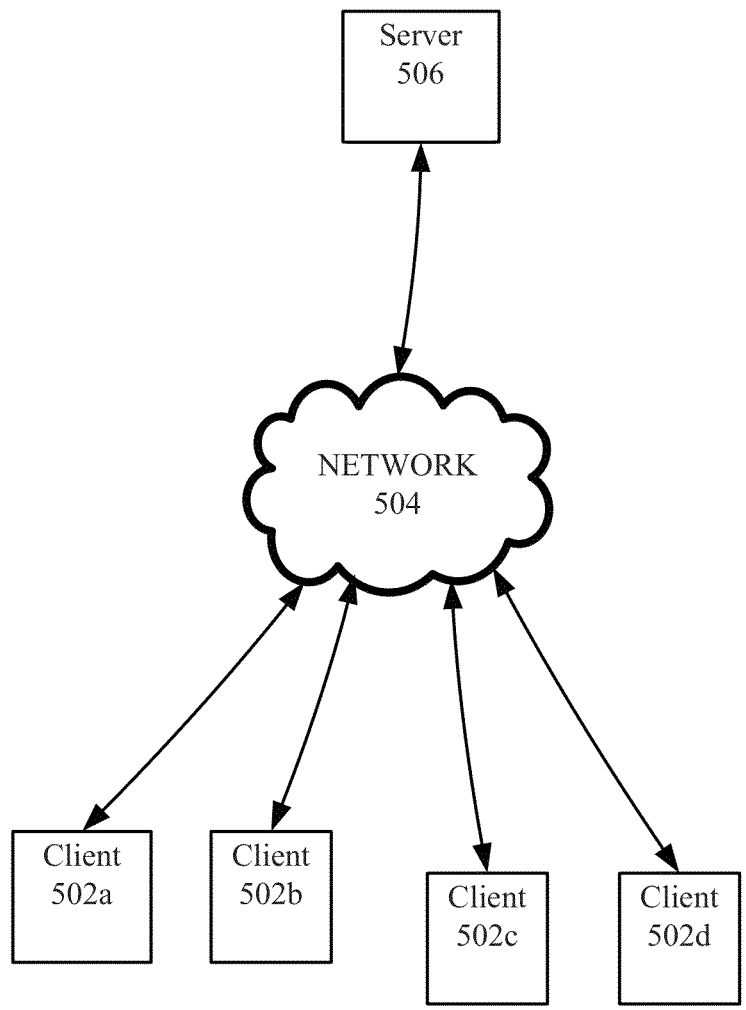
FIG. 5 illustrates a simplified diagram of a system, in accordance with various embodiments of the subject technology.

FIG. 5 illustrates a simplified diagram of a system 500, in accordance with various embodiments of the subject technology. The system 500 may include one or more remote client devices 502 (e.g., client devices 502a, 502b, 502c, and 502d) in communication with a server computing device 506 (server) via a network 504. In some embodiments, the server 506 is configured to run applications that may be accessed and controlled at the client devices 502. For example, a user at a client device 502 may use a web browser to access and control an application running on the server 506 over the network 504. In some embodiments, the server 506 is configured to allow remote sessions (e.g., remote desktop sessions) wherein users can access applications and files on the server 506 by logging onto the server 506 from a client device 502. Such a connection may be established using any of several well-known techniques such as the Remote Desktop Protocol (RDP) on a Windows-based server.

By way of illustration and not limitation, in one aspect of the disclosure, stated from a perspective of a server side (treating a server as a local device and treating a client device as a remote device), a server application is executed (or runs) at a server 506. While a remote client device 502 may receive and display a view of the server application on a display local to the remote client device 502, the remote client device 502 does not execute (or run) the server application at the remote client device 502. Stated in another way from a perspective of the client side (treating a server as remote device and treating a client device as a local device), a remote application is executed (or runs) at a remote server 506.

By way of illustration and not limitation, a client device 502 can represent a computer, a mobile phone, a laptop computer, a thin client device, a personal digital assistant (PDA), a portable computing device, or a suitable device with a processor. In one example, a client device 502 is a smartphone (e.g., iPhone, Android phone, Blackberry, etc.). In certain configurations, a client device 502 can represent an audio player, a game console, a camera, a camcorder, an audio device, a video device, a multimedia device, or a device capable of supporting a connection to a remote server. In one example, a client device 502 can be mobile. In another example, a client device 502 can be stationary. According to one aspect of the disclosure, a client device 502 may be a device having at least a processor and memory, where the total amount of memory of the client device 502 could be less than the total amount of memory in a server 506. In one example, a client device 502 does not have a hard disk. In one aspect, a client device 502 has a display smaller than a display supported by a server 506. In one aspect, a client device may include one or more client devices.

In some embodiments, a server 506 may represent a computer, a laptop computer, a computing device, a virtual machine (e.g., VMware® Virtual Machine), a desktop session (e.g., Microsoft Terminal Server), a published application (e.g., Microsoft Terminal Server) or a suitable device with a processor. In some embodiments, a server 506 can be stationary. In some embodiments, a server 506 can be mobile. In certain configurations, a server 506 may be any device that can represent a client device. In some embodiments, a server 506 may include one or more servers.

In one example, a first device is remote to a second device when the first device is not directly connected to the second device. In one example, a first remote device may be connected to a second device over a communication network such as a Local Area Network (LAN), a Wide Area Network (WAN), and/or other network.

When a client device 502 and a server 506 are remote with respect to each other, a client device 502 may connect to a server 506 over a network 504, for example, via a modem connection, a LAN connection including the Ethernet or a broadband WAN connection including DSL, Cable, T1, T3, Fiber Optics, Wi-Fi, or a mobile network connection including GSM, GPRS, 3G, WiMax or other network connection. A network 504 can be a LAN network, a WAN network, a wireless network, the Internet, an intranet or other network. A network 504 may include one or more routers for routing data between client devices and/or servers. A remote device (e.g., client device, server) on a network may be addressed by a corresponding network address, such as, but not limited to, an Internet protocol (IP) address, an Internet name, a Windows Internet name service (WINS) name, a domain name or other system name. These illustrate some examples as to how one device may be remote to another device. But the subject technology is not limited to these examples.

Figure 6:
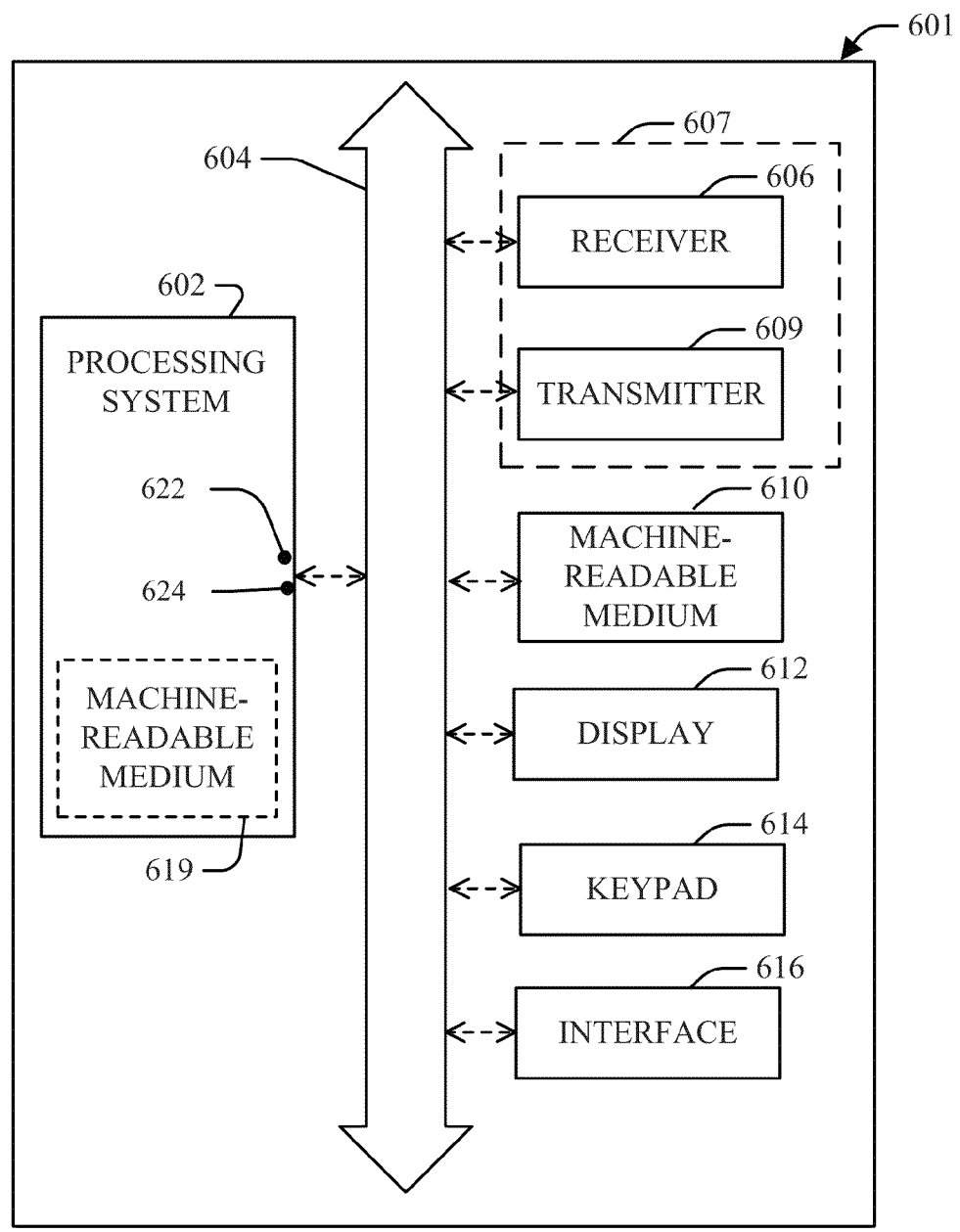
FIG. 6 is a conceptual block diagram illustrating an example of a system, in accordance with various embodiments of the subject technology.

FIG. 6 is a conceptual block diagram illustrating an example of a system, in accordance with various aspects of the subject technology. A system 601 may be, for example, a client device (e.g., client device 502) or a server (e.g., server 506) a remote client device in communication with a server computing device via a network. In other embodiments, the system 601 may be the remote client device or the server computing device. The system 601 may include a processing system 602. The processing system 602 is capable of communication with a receiver 606 and a transmitter 609 through a bus 604 or other structures or devices. It should be understood that communication means other than busses can be utilized with the disclosed configurations. The processing system 602 can generate audio, video, multimedia, and/or other types of data to be provided to the transmitter 609 for communication. In addition, audio, video, multimedia, and/or other types of data can be received at the receiver 606, and processed by the processing system 602.

The processing system 602 may include a processor for executing instructions and may further include a machine-readable medium 619, such as a volatile or non-volatile memory, for storing data and/or instructions for software programs. The instructions, which may be stored in a machine-readable medium 610 and/or 619, may be executed by the processing system 602 to control and manage access to the various networks, as well as provide other communication and processing functions. The instructions may also include instructions executed by the processing system 602 for various user interface devices, such as a display 612 and a keypad 614. The processing system 602 may include an input port 622 and an output port 624. Each of the input port 622 and the output port 624 may include one or more ports. The input port 622 and the output port 624 may be the same port (e.g., a bi-directional port) or may be different ports.

The machine-readable medium 610 and/or 619 can store instructions for performing the methods described herein, such as, for example method 100, method 200, and the methods described in the foregoing example.

The processing system 602 may be implemented using software, hardware, or a combination of both. By way of example, the processing system 602 may be implemented with one or more processors. A processor may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable device that can perform calculations or other manipulations of information.

A machine-readable medium can be one or more machine-readable media. Software shall be construed broadly to mean instructions, data, or any combination thereof, whether referred to as software, firmware, middleware, microcode, hardware description language, or otherwise. Instructions may include code (e.g., in source code format, binary code format, executable code format, or any other suitable format of code).

Machine-readable media (e.g., 619) may include storage integrated into a processing system, such as might be the case with an ASIC. Machine-readable media (e.g., 610) may also include storage external to a processing system, such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device. Those skilled in the art will recognize how best to implement the described functionality for the processing system 602. According to one aspect of the disclosure, a machine-readable medium is a computer-readable medium encoded or stored with instructions and is a computing element, which defines structural and functional interrelationships between the instructions and the rest of the system, which permit the instructions' functionality to be realized. In one aspect, a machine-readable medium is a non-transitory machine-readable medium, a machine-readable storage medium, or a non-transitory machine-readable storage medium. In one aspect, a computer-readable medium is a non-transitory computer-readable medium, a computer-readable storage medium, or a non-transitory computer-readable storage medium. Instructions may be executable, for example, by a client device or server or by a processing system of a client device or server. Instructions can be, for example, a computer program including code.

An interface 616 may be any type of interface and may reside between any of the components shown in FIG. 6. An interface 616 may also be, for example, an interface to the outside world (e.g., an Internet network interface). A transceiver block 607 may represent one or more transceivers, and each transceiver may include a receiver 606 and a transmitter 609. A functionality implemented in a processing system 602 may be implemented in a portion of a receiver 606, a portion of a transmitter 609, a portion of a machine-readable medium 610, a portion of a display 612, a portion of a keypad 614, or a portion of an interface 616, and vice versa.

According to certain embodiments of the subject technology, the terms "server" and "remote server" are generally used synonymously in relation to a client device, and the word "remote" may indicate that a server is in communication with other device(s), for example, over a network connection(s).

According to certain embodiments of the subject technology, the terms "client device" and "remote client device" are generally used synonymously in relation to a server, and the word "remote" may indicate that a client device is in communication with a server(s), for example, over a network connection(s).

In some embodiments, a "client device" may be sometimes referred to as a client or vice versa. Similarly, a "server" may be sometimes referred to as a server device or vice versa.

In some embodiments, the terms "local" and "remote" are relative terms, and a client device may be referred to as a local client device or a remote client device, depending on whether a client device is described from a client side or from a server side, respectively. Similarly, a server may be referred to as a local server or a remote server, depending on whether a server is described from a server side or from a client side, respectively. Furthermore, an application running on a server may be referred to as a local application, if described from a server side, and may be referred to as a remote application, if described from a client side.

In some embodiments, devices placed on a client side (e.g., devices connected directly to a client device(s) or to one another using wires or wirelessly) may be referred to as local devices with respect to a client device and remote devices with respect to a server. Similarly, devices placed on a server side (e.g., devices connected directly to a server(s) or to one another using wires or wirelessly) may be referred to as local devices with respect to a server and remote devices with respect to a client device.

In some embodiments, modules can be configured to perform the processes and functions described herein, such as, for example, the processes and functions of method 100, method 200, and the methods described in the foregoing example.

As used herein, the word "module" refers to logic embodied in hardware or firmware, or to a collection of software instructions, possibly having entry and exit points, written in a programming language, such as, for example C++. A software module may be compiled and linked into an executable program, installed in a dynamic link library, or may be written in an interpretive language such as BASIC. It will be appreciated that software modules may be callable from other modules or from themselves, and/or may be invoked in response to detected events or interrupts. Software instructions may be embedded in firmware, such as an EPROM or EEPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware.

It is contemplated that the modules may be integrated into a fewer number of modules. One module may also be separated into multiple modules. The described modules may be implemented as hardware, software, firmware or any combination thereof. Additionally, the described modules may reside at different locations connected through a wired or wireless network, or the Internet.

In general, it will be appreciated that the processors can include, by way of example, computers, program logic, or other substrate configurations representing data and instructions, which operate as described herein. In other embodiments, the processors can include controller circuitry, processor circuitry, processors, general purpose single-chip or multi-chip microprocessors, digital signal processors, embedded microprocessors, microcontrollers and the like.

Furthermore, it will be appreciated that in one embodiment, the program logic may advantageously be implemented as one or more components. The components may advantageously be configured to execute on one or more processors. The components include, but are not limited to, software or hardware components, modules such as software modules, object-oriented software components, class components and task components, processes methods, functions, attributes, procedures, subroutines, segments of program code, drivers, firmware, microcode, circuitry, data, databases, data structures, tables, arrays, and variables.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Moreover, a phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations which will be apparent to those skilled in the art may be made in the arrangement, operation and details of the method of the subject technology disclosed herein without departing from the spirit and scope of the subject technology as defined in the appended claims. Therefore, the scope of the subject technology should be determined by the appended claims and their legal equivalents. Furthermore, no element, component or method step is intended to be dedicated to the public regardless of whether the element, component or method step is explicitly recited in the claims. Underlined and/or italicized headings and subheadings are used for convenience only, do not limit the subject technology, and are not referred to in connection with the interpretation of the description of the subject technology. In the claims and description, unless otherwise expressed, reference to an element in the singular is not intended to mean "one and only one" unless explicitly stated, but rather is meant to mean "one or more." In addition, it is not necessary for a device or method to address every problem that is solvable by different embodiments of the disclosure in order to be encompassed by the claims.

What is claimed is:

1. A method for identifying bipolar disorder in a person who is 13 to 19 years old, comprising:

acquiring 31P spectroscopic data from a region of interest in a brain of the person;

by a processor, analyzing the data to obtain an indicator of each of a signal intensity and a concentration of inorganic phosphate (Pi); and determining, based on the indicators, at least one of a likely diagnosis of bipolar disorder or a probability of bipolar disorder in the person, the determining comprising comparing the indicated concentration of inorganic phosphate (Pi) to a threshold concentration of inorganic phosphate (Pi) obtained from 31P spectroscopic data acquired from persons not having bipolar disorder; and outputting, by a processor, an indicator of the at least one of the likely diagnosis or the probability.

2. The method of claim 1, further comprising outputting an indicator of a recommendation that a health care worker consider treating the person in view of the at least one of the likely diagnosis or the probability.

3. The method of claim 1, wherein the person is unmedicated for a mood disorder.

4. The method of claim 1, wherein the 31P spectroscopic data is obtained by magnetic resonance imaging.

5. The method of claim 1, wherein the indicated concentration of inorganic phosphate (Pi) is calculated as a percentage of a total phosphorus signal acquired from the region of interest.

6. The method of claim 1, wherein the region of interest is the frontal lobe of the brain.

7. A method of treating a person, comprising:

treating a person who is 13 to 19 years old, with at least one medication, based on at least one of a likely diagnosis of bipolar disorder or a probability of bipolar disorder in the person;

wherein the at least one of a likely diagnosis or the probability is derived from the following steps:

acquiring 31P spectroscopic data from a region of interest in the brain of the person;

by a processor, analyzing the data to obtain indicators of a signal intensity and a concentration of inorganic phosphate (Pi));

determining, based on the indicators of the concentration and the signal intensity, the at least one of the likely diagnosis or the probability, the determining comprising comparing the indicated concentration of inorganic phosphate (Pi) to a threshold concentration of inorganic phosphate (Pi) obtained from 31P spectroscopic data acquired from persons not having bipolar disorder.

8. The method of claim 7, wherein the person is unmedicated for a mood disorder when acquiring 31P spectroscopic data from the region of interest in the brain of the person.

9. The method of claim 7, wherein the indicated concentration of inorganic phosphate (Pi) is calculated as a percentage of a total phosphorus signal acquired from the region of interest.

10. A computer-implemented system for identifying bipolar disorder in a person who is 13 to 19 years old, the system comprising:

a processing module that processes 31P spectroscopic data, from a region of interest in a brain of the person, so as to obtain an indicator of each of a signal intensity and a concentration of inorganic phosphate (Pi);

a comparison module programmed to compare, by a processor, the concentration of inorganic phosphate (Pi) to a threshold concentration of inorganic phosphate (Pi) obtained from 31P spectroscopic data acquired from persons not having bipolar disorder; and an output module, in communication with the processing module, that outputs programmed to output, based on the indicators, a machine-readable indicator of at least one of a likely diagnosis of bipolar disorder or a probability of bipolar disorder in the person who is 13 to 19 years old.

11. The system of claim 10, wherein the person is unmedicated for a mood disorder.

\* \* \* \* \*